(12) United States Patent  (10) Patent No.: US 6,963,001 B2
Dershem et al.  (45) Date of Patent: Nov. 8, 2005

(54) LOW SHRINKAGE THERMOSETTING RESIN COMPOSITIONS AND METHODS OF USE THEREFOR

(75) Inventors: Stephen M. Dershem, San Diego, CA (US); Kang Yang, San Diego, CA (US); Puwei Liu, San Diego, CA (US)

(73) Assignee: Henkel Corporation, Rocky Hill, CT (US)

( * ) Notice: Subject to any disclaimer, the term of this patent is extended or adjusted under 35 U.S.C. 154(b) by 184 days.

(21) Appl. No.: 10/367,360

(22) Filed: Feb. 14, 2003

(65) Prior Publication Data

US 2004/0019224 A1 Jan. 29, 2004

Related U.S. Application Data

(63) Continuation-in-part of application No. 10/137,064, filed on Apr. 30, 2002, now Pat. No. 6,620,946, which is a continuation-in-part of application No. PCT/US01/30423, filed on Sep. 27, 2001.
(60) Provisional application No. 60/237,775, filed on Sep. 30, 2000.

(51) Int. Cl.$^7$ ............... C07D 209/56; C07D 207/12; C08K 2/46; C08J 9/00; C07F 126/08
(52) U.S. Cl. ............ 548/435; 546/544; 522/78; 521/79; 526/263; 524/502; 430/59
(58) Field of Search ............... 548/435, 544; 522/78; 521/79; 526/263; 524/502; 430/59; 560/254

(56) References Cited

U.S. PATENT DOCUMENTS

| | | | | |
|---|---|---|---|---|
| 3,369,058 A | * | 2/1968 | Keenan | 525/44 |
| 4,670,581 A | * | 6/1987 | Tanigaki | 560/108 |
| 4,837,197 A | * | 6/1989 | Ikeda et al. | 503/209 |
| 5,427,880 A | * | 6/1995 | Tamura et al. | 430/58.7 |
| 5,723,066 A | | 3/1998 | Coates et al. | |
| 5,948,847 A | * | 9/1999 | Iguchi et al. | 524/502 |
| 6,046,290 A | * | 4/2000 | Berneth et al. | 526/263 |
| 6,143,804 A | * | 11/2000 | Uejyukkoku et al. | 522/78 |
| 6,229,020 B1 | | 5/2001 | Shiono | |

* cited by examiner

Primary Examiner—Deborah C. Lambkin
(74) Attorney, Agent, or Firm—Steven C. Bauman (57) ABSTRACT

In accordance with the present invention, there are provided thermosetting resin compositions with a reduced propensity to shrink in volume upon cure and methods of use therefor. The compositions of the present invention include compounds having aromatic, rigid-rod like spacer groups between the crosslinkable moieties. As such, these compounds impart a degree of liquid crystal-like character to the thermosetting resin composition which results in lower shrinkage upon cure. This effect follows from the well-known expansion that occurs when liquid crystal-like materials pass from a nematic liquid crystal-like state to an isotropic state. Further provided by the present invention are low shrinkage die attach pastes and methods of use therefor.

40 Claims, 1 Drawing Sheet

Figure 1

LOW SHRINKAGE THERMOSETTING RESIN COMPOSITIONS AND METHODS OF USE THEREFOR

RELATED APPLICATIONS

This application is a continuation-in-part of U.S. patent application Ser. No. 10/137,064 filed Apr. 30, 2002 now U.S. Pat. No. 6,620,946, which claims priority to International Patent Application No. US01/30423, filed Sep. 27, 2001, which claims priority from U.S. Provisional Application No. 60/237,775, filed Sep. 30, 2000.

FIELD OF THE INVENTION

The present invention relates to thermosetting resin compositions and uses therefor. In particular, the present invention relates to compositions with markedly reduced shrinkage upon cure, thereby providing improved performance in adhesion applications. In a particular aspect, the present invention relates to die attach compositions useful for attaching semiconductor devices to carrier substrates.

BACKGROUND OF THE INVENTION

Thermosetting resins are commonly used in adhesive formulations due to the outstanding performance properties which can be achieved by forming a fully crosslinked (i.e., thermoset), three-dimensional network. These properties include cohesive bond strength, resistance to thermal and oxidative damage, and low moisture uptake. As a result, common thermosetting resins such as epoxy resins, bismaleimide resins, and cyanate ester resins have been employed extensively in applications ranging from structural adhesives (e.g., construction and aerospace applications) to microelectronics (e.g., die-attach and underfill applications).

Although thermosetting resins have been used successfully as adhesives in a variety of industries, a property inherent to all thermosetting resins which negatively impacts adhesion performance is shrinkage upon cure. This phenomenon is attributed to the formation of a three-dimensional, covalently crosslinked network during cure, which reduces intermolecular distances between the monomers used to form the crosslinked network. For example, before cure, the molecules which comprise the resin are separated by their characteristic van der Waal's radii. Upon cure, these intermolecular distances are reduced due to the formation of covalent bonds between monomers which produces the desired highly crosslinked thermoset material. This reduction of intermolecular distances creates internal stress throughout the thermoset network, which is manifested by reduced adhesion of the thermoset material to both the substrate and the object attached thereto.

It is well established that thermosetting monomers which cure via ring-opening chemistry (e.g., epoxies and benzoxazines) or ring-formation chemistry (e.g., cyanate esters) have reduced cure shrinkage. Ring-opening cure chemistry is advantageous since this physical transformation helps diminish volumetric shrinkage on cure. Similarly, ring-formation cure chemistry acts to reduce shrinkage due to the slight expansion which occurs upon ring-formation (much like that which occurs when water freezes to form ice crystals). Accordingly, epoxies, benzoxazines and cyanate esters all have excellent adhesive properties—presumably due to their diminished cure shrinkage. However, virtually all free-radically polymerized monomers do not participate in ring-opening or ring-forming reactions and therefore often exhibit severe cure shrinkage.

Strategies have been developed to address the problem of shrinkage upon cure. Common approaches include the addition of an inorganic filler to the adhesive formulation, and/or the use of a higher molecular weight thermosetting material. However, both of these strategies undesirably increase the viscosity of the final adhesive formulation. Accordingly, there remains a need for low shrinkage upon cure thermosetting resin compositions which do not detract from the properties of the adhesive formulation, in either its cured or uncured state, or its cure profile.

SUMMARY OF THE INVENTION

In accordance with the present invention, there are provided thermosetting resin compositions with a reduced propensity to shrink in volume upon cure and methods of use therefor. The compositions of the present invention include compounds having aromatic, rigid-rod like spacer groups between the crosslinkable moieties. As such, these compounds impart a degree of liquid crystal-like character to the thermosetting resin composition which results in lower shrinkage upon cure. This effect follows from the well-known expansion that occurs when liquid crystal-like materials pass from a nematic liquid crystal-like state to an isotropic state. Further provided by the present invention are low shrinkage formulations containing invention compounds and methods of use therefor.

DETAILED DESCRIPTION OF THE INVENTION

Thermosetting resin compositions of the present invention include compounds having the structure:

wherein:
  each Q is independently substituted or unsubstituted phenylene, substituted or unsubstituted cyclohexylene, substituted or unsubstituted naphthylene, substituted or unsubstituted heterocyclic, or combinations of any two or more thereof;
  each X is optional and, if present, is independently —O—, —S—, —SO—, —SO$_2$—, —S(O)$_2$—N(R)—, —CO—, —N(R)—, —CO$_2$—, —C(O)—N(R)—, —O—C(O)—O—, —O—C(O)—N(R)—, —N(R)—C(O)—N(R)—, —CR$_2$—, or substituted or unsubstituted lower heteroalkenylene, wherein R is —H or substituted or unsubstituted lower alkyl;
  each L is optional and, if present, is independently substituted or unsubstituted alkylene or substituted or unsubstituted oxyalkylene;
  each M is independently an ethylenically unsaturated crosslinkable moiety or saturated non-crosslinkable moiety;
  n and m are each independently an integer between 0–3, provided that one of m and n is at least 1; and
  k is 1 or 2.

As employed herein, the term "phenylene" refers to an optionally substituted, divalent 6-membered aromatic ring, the term "cyclohexylene" refers to an optionally substituted, divalent, saturated 6-membered ring, the term "naphthylene" refers to an optionally substituted, divalent 10 carbon fused aromatic ring system, and the term "heterocyclic" refers to optionally substituted, saturated or unsaturated, cyclic (i.e., ring-containing) groups containing one or more heteroatoms (e.g., N, O, S, or the like) as part of the ring structure, and having in the range of 3 up to 14 carbon atoms. Exemplary heterocyclic moieties include saturated rings, unsaturated rings, and aromatic heteroatom-containing ring systems such as epoxy, tetrahydrofuran, oxazoline, oxazine, pyrrole, pyridine, furan, and the like.

Combinations of the above include two or more of the same or different moieties from among those listed. Thus, where Q is a combination, it may be, for example, two phenylenes such as biphenyl, an unsubstituted phenylene and a substituted phenylene such as diphenylmethyl, and the like.

As employed herein, the term "substituted", when used in conjunction with any of the species referred to herein, includes substituents such as hydroxy, alkyl, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, oxo, amino, amido, maleimido, succinimido, itaconimido, —C(O)H, acyl, oxyacyl, carboxyl, carbamate, sulfonyl, sulfonamide, sulfuryl, and the like.

As employed herein, "alkyl" refers to saturated straight or branched chain hydrocarbon radical having in the range of 1 up to about 500 carbon atoms. "Lower alkyl" refers to straight or branched chain alkyl radicals having in the range of about 1 up to 4 carbon atoms. "Substituted alkyl" refers to alkyl groups further bearing one or more substituents as set forth above.

Figure 1:
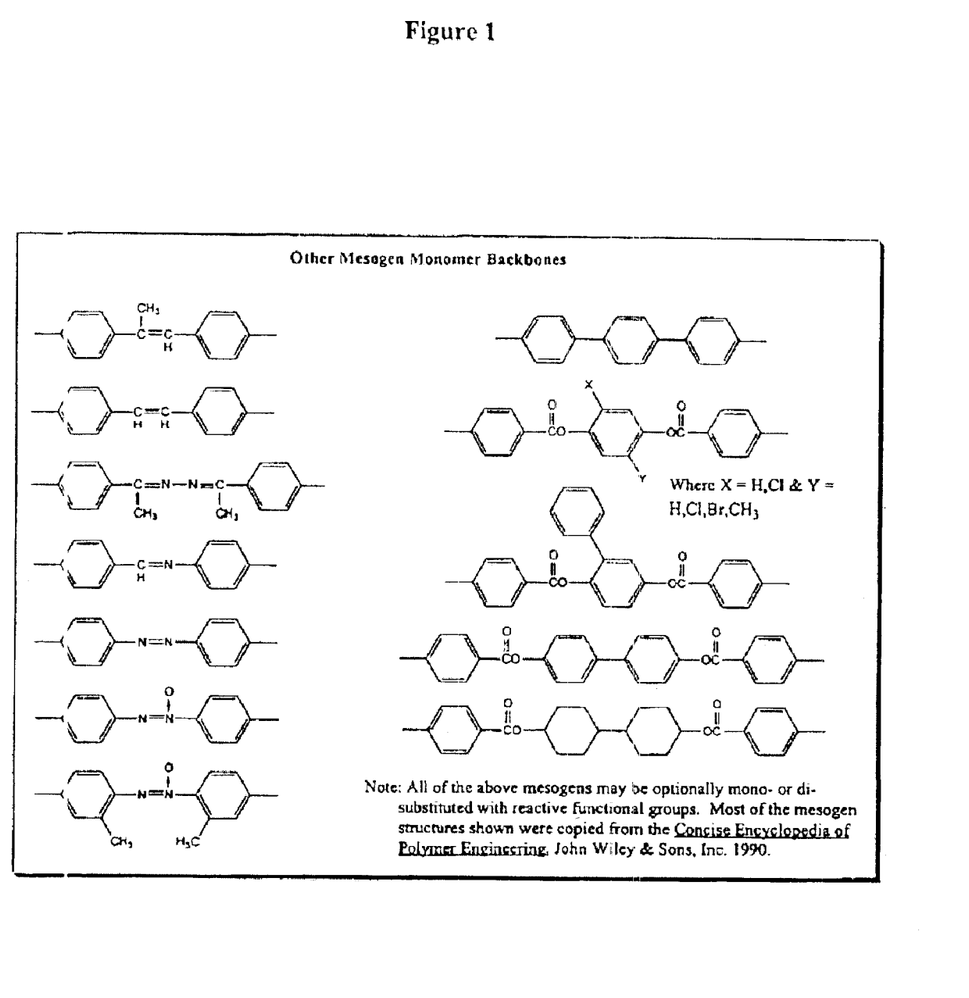
FIG. 1 illustrates several exemplary structures which can be incorporated into compounds contemplated by the present invention.

As employed herein, the term "lower heteroalkenylene" refers to divalent, straight or branched chain spacer groups having in the range of about 1 up to 4 carbon atoms and/or heteroatoms, and wherein the spacer groups contain at least one double bond. Examples of such groups are illustrated in FIG. 1.

As employed herein, the term "heteroatom" refers to N, O, S, or P.

As employed herein, the term "cycloalkyl" refers to cyclic ring-containing groups containing in the range of 3 up to about 20 carbon atoms, and "substituted cycloalkyl" refers to cycloalkyl groups further bearing one or more substituents as set forth above.

As employed herein, "alkylene" refers to saturated, divalent straight or branched chain hydrocarbyl groups typically having in the range of 1 up to about 500 carbon atoms, and "substituted alkylene" refers to alkylene groups further bearing one or more substituents as set forth above.

As employed herein, "oxyalkylene" refers to divalent, straight or branched chain moieties which contain at least one oxygen atom within the hydrocarbon backbone.

As employed herein, the term "saturated non-crosslinkable moiety" refers to hydrocarbon moieties which have no polymerizable double bonds, and therefore do not react with a curing catalyst under pre-determined curing conditions.

As employed herein, the term "ethylenically unsaturated crosslinkable moiety" refers to a moiety which reacts with a curing catalyst under pre-determined curing conditions, wherein the moiety has at least one unit of ethylenic unsaturation. As employed herein, "ethylenic unsaturation" refers to a polymerizable (i.e., non-aromatic) carbon—carbon double bond, as shown below:

In some embodiments the present invention includes compounds having the general structure described above, wherein M is an ethylenically unsaturated crosslinkable moiety. Unsaturated moieties contemplated for use in the practice of the present invention include unsaturated anhydride groups, (meth)acrylate groups, maleimide groups, nadimide groups, itaconimide groups, styrene groups, vinyl ester groups, vinyl ether groups, divinyl groups, and the like. In some such embodiments, M is a (meth)acrylate group, maleimide group, nadimide group, or itaconimide group.

As employed herein, the term "(meth)acrylate group" refers to moieties having the structure:

wherein $R^1$ is H or optionally substituted alkyl.

As employed herein, the term "maleimide group" refers to moieties having the structure:

wherein $R^1$ is —H or optionally substituted alkyl.

As employed herein, the term "nadimide group" refers to moieties having the structure:

wherein p=0–15.

As employed herein, the term "itaconimide group" refers to moieties having the structure:

Preferred embodiments according to the present invention include compounds having the general structure set forth above, wherein Q is phenylene, m is 0, k is 1, and n is 1, resulting in compounds which have the structure:

One embodiment according to the present invention includes compounds having the general structure set forth above, wherein X is O, L is methylene, and M is an ethylenically unsaturated crosslinkable moiety such as, for example, a (meth)acrylate group, maleimide group, nadimide group, or itaconimide group, resulting in compounds which have the structures:

wherein p = 0–15 amd $R^1$ is ——H or optionally substitued alkyl.

Additional specific embodiments according to the present invention include compounds having the general structure set forth above, wherein Q is phenylene, X is absent, m is 0, and k is 1, resulting in compounds which have the following structures:

while R is is —H or optionally substituted alkyl, b=1=10, and p=0–15.

While the substituents on the phenylene groups shown above are in the 1,4 positions, they may also occur at other positions on the phenylene ring, e.g., 1,2 or 1,3.

In an alternative embodiment, compounds contemplated for use in the practice of the present invention include compounds having the general structure set forth below wherein X and L are as defined above and M is a saturated non-crosslinkable moiety. Saturated moieties contemplated for use in the practice of the present invention include, for example, alkylcarboxylate groups, alkyl ether groups, aryl ether groups, succinimido groups, alkyl carbonyl groups, aryl carbonyl groups, and the like.

As employed herein, the term "alkylcarboxylate group" refers to moieties having the structure:

wherein R' is an optionally substituted alkyl or cycloalkyl.

As employed herein, the term "succinimido group" refers to moieties having the structure:

In certain specific embodiments of the present invention, X is O, L is methylene, and M is succinimido group or —(C=O)—CH($R^1$)($CH_3$), wherein $R^1$ is hydrogen or optionally substituted alkyl.

Additional specific embodiments contemplated according to this aspect of the present invention include compounds having the general structure set forth above, wherein Q is phenylene, X is absent, m is 0, n is 1, and k is 1, resulting in compounds having the structures set forth below:

wherein R is —H or optionally substitued alkyl and b = 1–10.

In addition to reduced shrinkage upon cure, the compounds contemplated for use herein provide further benefits when incorporated into a thermosetting resin composition. For example, the present compounds can be used to improve hydrophobicity of the resin and to reduce bleed on a variety of substrates, while maintaining low volatility of the overall composition.

In another aspect of the invention, the compositions of the present invention further include a maleimide, a nadimide, an itaconimide, a coupling agent, a curing catalyst, or any combination thereof. Maleimides, nadimides, and itaconimides contemplated by the present invention have, respectively, the structures I, II and III:

wherein:
m=1–15,
p=0–15,
each $R^2$ is independently selected from hydrogen or lower alkyl, and
J is a monovalent or a polyvalent moiety comprising organic or organosiloxane radicals, and combinations of any two or more thereof.

In one aspect of the invention, J is of sufficient length and branching to render the maleimide, nadimide, or itaconimide, respectively, in the liquid state at room temperature.

Monovalent moieties or polyvalent moieties are typically selected from hydrocarbyl, substituted hydrocarbyl, heteroatom-containing hydrocarbyl, substituted heteroatom-containing hydrocarbyl, hydrocarbylene, substituted hydrocarbylene, heteroatom-containing hydrocarbylene, substituted heteroatom-containing hydrocarbylene, polysiloxane, polysiloxane-polyurethane block copolymer, or combinations of two or more thereof, optionally containing one or more linkers selected from the group consisting of a covalent bond, —O—, —S—, —NR—, —O—C(O)—, —O—C(O)—O—, —O—C(O)—NR—, —NR—C(O)—, —NR—C(O)—O—, —NR—C(O)—NR—, —S—C(O)—, —S—C(O)—O—, —S—C(O)—NR—, —O—S(O)$_2$—, —O—S(O)$_2$—O—, —O—S(O)$_2$—NR—, —O—S(O)—, —O—S(O)—O—, —O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR—, —NR—C(S)—, —NR—C(S)—O—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—O—, —NR—O—S(O)$_2$—NR—, —O—NR—S(O)—, —O—NR—S(O)—O—, —O—NR—S(O)—NR—, —O—NR—S(O)$_2$—O—, —O—NR—S(O)$_2$—NR—, —O—NR—S(O)$_2$—, —O—P(O)R$_2$—, —S—P(O)R$_2$—, —NR—P(O)R$_2$—, wherein each R is independently hydrogen, alkyl or substituted alkyl, and combinations of any two or more thereof.

As employed herein, "hydrocarbyl" comprises any organic radical wherein the backbone thereof comprises carbon and hydrogen only. Thus, hydrocarbyl embraces alkyl, cycloalkyl, alkenyl, cycloalkenyl, alkynyl, aryl, alkylaryl, arylalkyl, arylalkenyl, alkenylaryl, arylalkynyl, alkynylaryl, and the like. "Substituted hydrocarbyl" refers to hydrocarbyl groups further bearing one or more substituents as set forth above.

As employed herein, "alkenyl" refers to straight or branched chain hydrocarbyl groups having at least one carbon—carbon double bond, and typically having in the range of about 2 up to 500 carbon atoms, and "substituted alkenyl" refers to alkenyl groups further bearing one or more substituents as set forth above.

As employed herein, "cycloalkenyl" refers to cyclic ring-containing groups containing in the range of about 3 up to 20 carbon atoms and having at least one carbon-carbon double bond, and "substituted cycloalkenyl" refers to cycloalkenyl groups further bearing one or more substituents as set forth above.

As employed herein, "alkynyl" refers to straight or branched chain hydrocarbyl groups having at least one carbon—carbon triple bond, and typically having in the range of about 2 up to 500 carbon atoms, and "substituted alkynyl" refers to alkynyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "arylalkyl" refers to aryl-substituted alkyl groups and "substituted arylalkyl" refers to arylalkyl groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "alkenylaryl" refers to alkenyl-substituted aryl groups and "substituted alkenylaryl" refers to alkenylaryl groups further bearing one or more substituents as set forth above.

As employed herein, "arylalkynyl" refers to aryl-substituted alkynyl groups and "substituted arylalkynyl" refers to arylalkynyl groups further bearing one or more substituents as set forth above.

As employed herein, "alkynylaryl" refers to alkynyl-substituted aryl groups and "substituted alkynylaryl" refers to alkynylaryl groups further bearing one or more substituents as set forth above.

As employed herein, "hydrocarbylene" refers to divalent straight or branched chain hydrocarbyl groups including alkylene groups, alkenylene groups, alkynylene groups, cycloalkylene groups, heterocycloalkylene groups, arylene groups, alkylarylene groups, arylalkylene groups, arylalkenylene groups, arylalkynylene groups, alkenylarylene groups, alkynylarylene groups, and the like; and "substituted hydrocarbylene" refers to hydrocarbylene groups further bearing one or more substituents as set forth above.

As employed herein, "alkenylene" refers to divalent straight or branched chain hydrocarbyl groups having at least one carbon—carbon double bond, and typically having in the range of about 2 up to 500 carbon atoms, and "substituted alkenylene" refers to alkenylene groups further bearing one or more substituents as set forth above.

As employed herein, "alkynylene" refers to divalent straight or branched chain hydrocarbyl groups having at least one carbon—carbon triple bond, and typically having in the range of about 2 up to 500 carbon atoms, and "substituted alkynylene" refers to alkynylene groups further bearing one or more substituents as set forth above.

As employed herein, "cycloalkylene" refers to divalent ring-containing groups containing in the range of 3 up to about 20 carbon atoms, and "substituted cycloalkylene" refers to cycloalkylene groups further bearing one or more substituents as set forth above.

As employed herein, "heterocycloalkylene" refers to divalent cyclic (i.e., ring-containing) groups containing one or more heteroatoms (e.g., N, O, S, or the like) as part of the ring structure, and having in the range of 1 up to about 14 carbon atoms and "substituted heterocycloalkylene" refers to heterocycloalkylene groups further bearing one or more substituents as set forth above.

As employed herein, "cycloalkenylene" refers to divalent ring-containing groups containing in the range of 3 up to about 20 carbon atoms and having at least one carbon-carbon double bond, and "substituted cycloalkenylene" refers to cycloalkenylene groups further bearing one or more substituents as set forth above.

As employed herein, "arylene" refers to divalent aromatic groups typically having in the range of 6 up to 14 carbon atoms and "substituted arylene" refers to arylene groups further bearing one or more substituents as set forth above.

As employed herein, "alkylarylene" refers to alkyl-substituted divalent aryl groups typically having in the range of about 7 up to 16 carbon atoms and "substituted alkylarylene" refers to alkylarylene groups further bearing one or more substituents as set forth above.

As employed herein, "arylalkylene" refers to aryl-substituted divalent alkyl groups typically having in the range of about 7 up to 16 carbon atoms and "substituted arylalkylene" refers to arylalkylene groups further bearing one or more substituents as set forth above.

As employed herein, "arylalkenylene" refers to aryl-substituted divalent alkenyl groups typically having in the range of about 8 up to 16 carbon atoms and "substituted arylalkenylene" refers to arylalkenylene groups further bearing one or more substituents as set forth above.

As employed herein, "arylalkynylene" refers to aryl-substituted divalent alkynyl groups typically having in the range of about 8 up to 16 carbon atoms and "substituted arylalkynylene" refers to arylalkynylene group further bearing one or more substituents as set forth above.

As employed herein, "alkenylarylene" refers to alkenyl-substituted divalent aryl groups typically having in the range of about 7 up to 16 carbon atoms and "substituted alkenylarylene" refers to alkenylarylene groups further bearing one or more substituents as set forth above.

As employed herein, "alkynylarylene" refers to alkynyl-substituted divalent aryl groups typically having in the range of about 7 up to 16 carbon atoms and "substituted alkynylarylene" refers to alkynylarylene groups further bearing one or more substituents as set forth above.

As employed herein, "polysiloxane-polyurethane block copolymers" refer to polymers containing both at least one polysiloxane (soft) block and at least one polyurethane (hard) block.

When one or more of the above described monovalent or polyvalent groups contain one or more of the above described linkers to form the "J" appendage of a maleimide, nadimide or itaconimide group, as readily recognized by those of skill in the art, a wide variety of organic chains can be produced, such as, for example, oxyalkyl, thioalkyl, aminoalkyl, carboxylalkyl, oxyalkenyl, thioalkenyl, aminoalkenyl, carboxyalkenyl, oxyalkynyl, thioalkynyl, aminoalkynyl, carboxyalkynyl, oxycycloalkyl, thiocycloalkyl, aminocyclo alkyl, carboxycycloalkyl, oxycloalkenyl, thiocycloalkenyl, aminocycloalkenyl, carboxycycloalkenyl, heterocyclic, oxyheterocyclic, thioheterocyclic, aminoheterocyclic, carboxyheterocyclic, oxyaryl, thioaryl, aminoaryl, carboxyaryl, heteroaryl, oxyheteroaryl, thioheteroaryl, aminoheteroaryl, carboxyheteroaryl, oxyalkylaryl, thioalkylaryl, aminoalkylaryl, carboxyalkylaryl, oxyarylalkyl, thioarylalkyl, aminoarylalkyl, carboxyarylalkyl, oxyarylalkenyl, thioarylalkenyl, aminoarylalkenyl, carboxyarylalkenyl, oxyalkenylaryl, thioalkenylaryl, aminoalkenylaryl, carboxyalkenylaryl, oxyarylalkynyl, thioarylalkynyl, aminoarylalkynyl, carboxyarylalkynyl, oxyalkynylaryl, thioalkynylaryl, aminoalkynylaryl or carboxyalkynylaryl, oxyalkylene, thioalkylene, aminoalkylene, carboxyalkylene, oxyalkenylene, thioalkenylene, aminoalkenylene, carboxyalkenylene, oxyalkynylene, thioalkynylene, aminoalkynylene, carboxyalkynylene, oxycycloalkylene, thiocycloalkylene, aminocycloalkylene, carboxycycloalkylene, oxycycloalkenylene, thiocycloalkenylene, aminocycloalkenylene, carboxycycloalkenylene, oxyarylene, thioarylene, aminoarylene, carboxyarylene, oxyalkylarylene, thioalkylarylene, aminoalkylarylene, carboxyalkylarylene, oxyarylalkylene, thioarylalkylene, aminoarylalkylene, carboxyarylalkylene, oxyarylalkenylene, thioarylalkenylene, aminoarylalkenylene, carboxyarylalkenylene, oxyalkenylarylene, thioalkenylarylene, aminoalkenylarylene, carboxyalkenylarylene, oxyarylalkynylene, thioarylalkynylene, aminoarylalkynylene, carboxy arylalkynylene, oxyalkynylarylene, thioalkynylarylene, aminoalkynylarylene, carboxyalkynylarylene, heteroarylene, oxyheteroarylene, thioheteroarylene, aminoheteroarylene, carboxyheteroarylene, heteroatom-containing di- or polyvalent cyclic moiety, oxyheteroatom-containing di- or polyvalent cyclic moiety, thioheteroatom-containing di- or polyvalent cyclic moiety, aminoheteroatom-containing di- or polyvalent cyclic moiety, carboxyheteroatom-containing di- or polyvalent cyclic moiety, and the like.

As employed herein, "heteroarylene" refers to divalent aromatic groups containing one or more heteroatoms (e.g., N, O, S or the like) as part of the aromatic ring, and typically having in the range of 3 up to about 14 carbon atoms and "substituted heteroarylene" refers to heteroarylene groups further bearing one or more substituents as set forth above.

In another embodiment, maleimides, nadimides, and itaconimides contemplated for use in the practice of the present invention have the structures I, II, or III wherein, m=1–6, p=0–6, and J is (a) saturated straight chain alkyl or branched chain alkyl, optionally containing substituents selected from hydroxy, alkoxy, carboxy, nitrile, cycloalkyl cycloalkenyl, or optionally substituted aryl moieties as substituents on the alkyl chain or as part of the backbone of the alkyl chain, and wherein the alkyl chains have up to about 20 carbon atoms;

(b) alkylene, oxyalkylene, alkenyl, alkenylene, oxyalkenylene, ester, or polyester, optionally containing substituents selected from hydroxy, alkoxy, carboxy, nitrile, cycloalkyl or cycloalkenyl;

(c) a siloxane having the structure $-(C(R^3)_2)_d-[Si(R^4)_2-O]_f-Si(R^4)_2-(C(R^3)_2)_e-$, $-(C(R^3)_2)_d-C(R^3)-C(O)O-(C(R^3)_2)_d-[Si(R^4)_2-O]_f-Si(R^4)_2-(C(R^3)_2)_e-O(O)C-(C(R^3)_2)_e-$, or $-(C(R_3)_2)_d-C(R^3)-O(O)C-(C(R^3)_2)_d-[Si(R^4)_2-O]_f-Si(R^4)_2-(C(R^3)_2)_e-C(O)O-(C(R^3)_2)_e-$ wherein, each $R^3$ is independently hydrogen, alkyl or substituted alkyl, each $R^4$ is independently hydrogen, lower alkyl or aryl, d=1–10, e=1–10, and f=1–50;

(d) a polyalkylene oxide having the structure:

wherein:

each R is independently hydrogen, alkyl or substituted alkyl, r=1–10, s=1–10, and f is as defined above;

(e) aromatic groups having the structure:

wherein each Ar is a monosubstituted, disubstituted or trisubstituted aromatic or heteroaromatic ring having in the range of 3 up to 10 carbon atoms, and Z is:

(i) saturated straight chain alkylene or branched chain alkylene, optionally containing saturated cyclic moieties as substituents on the alkylene chain or as part of the backbone of the alkylene chain, or (ii) polyalkylene oxides having the structure:

wherein:

each R is independently defined as above, r=1–10, s=1–10, and q=1–50;

(f) di- or tri-substituted aromatic moieties having the structure:

wherein:
each R is independently defined as above,
t=2–10,
a=2–10, and
Ar is as defined above;
(g) aromatic groups having the structure:

wherein:
t=is as defined above,
u=1, 2 or 3,
g=1 up to about 50,
each R is independently defined as above,
each Ar is as defined above,
E is —O— or —NR$^5$—, wherein R$^5$ is hydrogen or lower alkyl;
and
W is
(i) straight or branched chain alkyl, alkylene, oxyalkylene, alkenyl, alkenylene, oxyalkenylene, ester, or polyester, optionally containing substituents selected from hydroxy, alkoxy, carboxy, nitrile, cycloalkyl or cycloalkenyl,
(ii) a siloxane having the structure —(C(R$^3$)$_2$)$_d$—[Si(R$^4$)$_2$—O]$_f$—Si(R$^4$)$_2$—(C(R$^3$)$_2$)$_e$—, —(C(R$^3$)$_2$)$_e$—, —(C(R$^3$)$_2$)$_d$—C(R$^3$)—C(O)O—(C(R$^3$)$_2$)$_d$—[Si(R$^4$)$_2$—O]$_f$—Si(R$^4$)$_2$—(C(R$^3$)$_2$)$_e$—O(O)C—(C(R$^3$)$_2$)$_e$—, or —(C(R$^3$)$_2$)$_d$—C(R$^3$)—O(O)C—(C(R$^3$)$_2$)$_d$—[Si(R$^4$)$_2$—O]$_f$—Si(R$^4$)$_2$—(C(R$^3$)$_2$)$_e$—C(O)O—(C(R$^3$)$_2$)$_e$— wherein,
each R$^3$ is independently hydrogen, alkyl or substituted alkyl,
each R$^4$ is independently hydrogen, lower alkyl or aryl,
d=1–10,
e=1–10, and
f=1–50; or
(iii) a polyalkylene oxide having the structure:

wherein:
each R is independently defined as above,
r=1–10,
s=1–10, and
f is defined as above;
optionally containing substituents selected from hydroxy, alkoxy, carboxy, nitrile, cycloalkyl or cycloalkenyl;

(h) a urethane group having the structure:

wherein:
each R$^6$ is independently hydrogen or lower alkyl;
each R$^7$ is independently an alkyl, aryl, or arylalkyl group having 1 to 18 carbon atoms;
each R$^8$ is an alkyl or alkyloxy chain having up to about 100 atoms in the chain, optionally substituted with Ar;
U is —O—, —S—, —N(R)—, or —P(L)$_{1,2}$— wherein R as defined above, and wherein each L is independently =O, =S, —OR or —R; and
v=0–50;
(i) polycyclic alkenyl; or
(j) mixtures of any two or more thereof.

The attachment point(s) of the J moiety to the maleimide(s), nadimide(s) or itaconimide(s) are understood to be at any atom(s) of the J moiety having sufficient valence to accommodate such attachment. Thus, for example, any C—H, N—H, O—H, or S—H bond may be replaced by a bond between the non-hydrogen atom and the maleimide, nadimide or itaconimide.

Preferred maleimides, nadimides, and itaconimides contemplated for use in the practice of the present invention are those which exist as liquids at ambient temperature, as noted above. Presently preferred liquid maleimides, nadimides, and itaconimides include compounds wherein J contains 12–500 carbon atoms. Most preferred liquid maleimides, nadimides, and itaconimides include compounds wherein J contains 20–100 carbon atoms.

As employed herein, the term "cure initiator" refers to any chemical species which, upon exposure to sufficient energy (e.g., light, heat, or the like), catalyzes the crosslinking polymerization reaction which converts the functionalized monomeric compounds (contained within the overall composition) into a three-dimensional thermoset network. For example, when exposed to sufficient energy a free radical cure initiator decomposes into two parts which are uncharged, but which each possess at least one unpaired electron. Preferred as free radical initiators for use in the practice of the present invention are compounds which decompose (i.e., have a half life in the range of about 10 hours) at temperatures in the range of about 70 up to about 180° C. Exemplary free radical initiators contemplated for use in the practice of the present invention include peroxides (e.g., dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, and tert-butyl hydroperoxide), azo compounds (e.g., 2,2'-azobis(2-methyl-propanenitrile), 2,2'-azobis(2-methylbutanenitrile), and 1,1'-zobis (cyclohexanecarbonitrile)), and the like.

Peroxide initiators are presently preferred because they generate no gas release upon decomposition into free radicals. Those of skill in the art recognize, however, that in certain adhesive applications, the release of gas (e.g., N$_2$) during cure of the adhesive would be of no real concern. Generally in the range of about 0.2 up to 3 wt % of at least one free radical initiator (based on the total weight of the organic phase) will be employed, with in the range of about 0.5 up to 1.5 wt % preferred.

As employed herein, the term "coupling agent" refers to chemical species that are capable of bonding to a mineral surface and which also contain polymerizably reactive functional group(s) so as to enable interaction with the adhesive composition. Coupling agents thus facilitate linkage of the adhesive composition to the substrate to which it is applied.

Exemplary coupling agents contemplated for use in the practice of the present invention includes silicate esters, metal acrylate salts (e.g., aluminum methacrylate), titanates (e.g., titanium methacryloxyethylacetoacetate triisopropoxide), or compounds that contain a copolymerizable group and a chelating ligand (e.g., phosphine, mercaptan, acetoacetate, and the like). Generally in the range of about 0.1 up to about 10 wt % of at least one coupling agent (based on the total weight of the organic phase) will be employed, with in the range of about 0.5 up to about 2 wt % preferred.

Presently preferred coupling agents contain both a co-polymerizable function (e.g., vinyl moiety, acrylate moiety, methacrylate moiety, and the like), as well as a silicate ester function. The silicate ester portion of the coupling agent is capable of condensing with metal hydroxides present on the mineral surface of substrate, while the co-polymerizable function is capable of co-polymerizing with the other reactive components of invention adhesive composition. Especially preferred coupling agents contemplated for use in the practice of the invention are oligomeric silicate coupling agents such as poly (methoxyvinylsiloxane).

In accordance with another aspect of the invention, invention compositions further include acrylate derivatives of oligomers of optionally substituted cyclopentadiene.

In accordance with still another aspect of the invention, there are provided formulations containing invention compounds. Such formulations can be used in a variety of applications, e.g., underfill, die attach, encapsulation, molding compounds, and the like. For example, when employed for the preparation of die-attach pastes, such formulations include:

in the range of about 10 up to about 80 wt % of the above-described adhesive composition, and in the range of about 20 up to about 90 wt % filler.

Fillers contemplated for use in the practice of the present invention can be electrically conductive and/or thermally conductive, and/or fillers having no appreciable conductivity, whose function is primarily to modify the rheology of the resulting composition. Examples of suitable electrically conductive fillers which can be employed in the practice of the present invention include silver, nickel, copper, aluminum, palladium, gold, graphite, metal-coated graphite (e.g., nickel-coated graphite, copper-coated graphite, and the like), and the like. Examples of suitable thermally conductive fillers which can be employed in the practice of the present invention include graphite, aluminum nitride, silicon carbide, boron nitride, diamond dust, alumina, and the like. Compounds which act primarily to modify rheology include fumed silica, alumina, titania, and the like.

In accordance with yet another embodiment of the present invention, there are provided assemblies of components adhered together employing the above-described adhesive compositions and/or die attach compositions. Thus, for example, assemblies including a first article permanently adhered to a second article by a cured aliquot of the above-described adhesive composition are provided. Articles contemplated for assembly employing invention compositions include memory devices, ASIC devices, microprocessors, flash memory devices, and the like.

The invention further provides methods for reducing the shrinkage upon cure of a thermosetting resin composition, where the method includes combining the resin with the above described compounds of the invention. Some such embodiments further include in the thermosetting resin composition, the above-described maleimides, nadimides, and itaconimides, or combinations of any two or more thereof having, respectively, the structures I, II and III.

Also contemplated are assemblies comprising a microelectronic device permanently adhered to a substrate by a cured aliquot of the above-described die attach paste. Microelectronic devices contemplated for use with invention die attach pastes include copper lead frames, Alloy 42 lead frames, silicon dice, gallium arsenide dice, germanium dice, and the like.

In accordance with still another embodiment of the present invention, there are provided methods for adhesively attaching two component parts to produce the above-described assemblies. Thus, for example, a first article can be adhesively attached to a second article, employ a method comprising:

(a) applying the above-described adhesive composition to the first article, (b) bringing the first and second article into intimate contact to form an assembly wherein the first article and the second article are separated only by the adhesive composition applied in step (a), and thereafter, (c) subjecting the assembly to conditions suitable to cure the adhesive composition.

Similarly, a microelectronic device can be adhesively attached to a substrate, employing a method comprising:

(a) applying the above-described die attach paste to the substrate and/or the microelectronic device, (b) bringing the substrate and the device into intimate contact to form an assembly wherein the substrate and the device are separated only by the die attach composition applied in step (a), and thereafter, (c) subjecting the assembly to conditions suitable to cure the die attach composition.

Conditions suitable to cure invention die attach compositions comprise subjecting the above-described assembly to a temperature of less than about 200° C. for about 0.5 up to about 2 minutes. This rapid, short duration heating can be accomplished in a variety of ways, e.g., with an in-line heated rail, a belt furnace, or the like.

The present invention also provides adhesive film compositions suitable for use in die-attach and other applications. Such compositions comprise a thermoset resin, as described above, and a thermoplastic elastomer. The latter is a block copolymer having at least one unit of the general formula (A-B) or (A-B-A), wherein A is a non-elastomeric polymer block and B is an elastomeric polymer block that is the polymerization product of optionally substituted olefin monomers and/or optionally substituted conjugated diene monomers.

As employed herein, the term "block copolymer" refers to polymers composed of two or more different polymer subunits joined together. An elastomeric polymer block is a polymer subunit that exhibits rubber-like properties; i.e. it is soft at room temperature and deforms under stress but recovers upon the removal of stress. A non-elastomeric polymer block is a polymer subunit that is hard at room temperature and does not stretch. Polybutadiene is an example of an elastomeric polymer block, while polystyrene is an example of a non-elastomeric block.

Thermoplastic elastomers contemplated for use in the practice of the present invention include, for example, polystyrene-polybutadiene-polystyrene block copolymers, polystyrene-polyisoprene-polystyrene block copolymers, polystyrene-polydimethylbutadiene-polystyrene block copolymers, polybutadiene-polyacrylonitrile block copolymers, and the like. Preferably, the block copolymer is a polystyrene-polybutadiene-polystyrene block copolymer or a polybutadiene-polyacrylonitrile block copolymer.

In a further aspect of the invention, there are provided assemblies employing such adhesive film formulations and methods for making the same. Thus the invention provides methods for adhesively attaching a device to a substrate comprising subjecting a sufficient quantity of an invention adhesive composition positioned between a substrate and a device to conditions suitable to cure the adhesive formulation. Devices contemplated for use in the practice of the present invention include any surface mount component such as, for example, semiconductor die, resistors, capacitors, and the like. Preferably, devices contemplated for use in the practice of invention methods are semiconductor dies. Substrates contemplated for use include metal substrates (e.g., lead frames), organic substrates (e.g., laminates, ball grid arrays, polyamide films), and the like.

Various conditions are suitable to cure invention adhesive film compositions. For example, some embodiments comprise subjecting invention film adhesive compositions to a temperature of at least about 150° C. but less than about 300° C. for about 0.5 up to about 2 minutes. This rapid, short duration heating can be accomplished in a variety of ways, e.g., with an in-line heated rail, a belt furnace, or the like. Alternative embodiments comprise subjecting invention film adhesive compositions to a temperature in the range of about 120° C. up to about 200° C. for a period of about 15 minutes up to about 60 minutes. These conditions can be readily produced in a variety of ways, such as, for example, by placing invention film adhesive compositions in a curing oven. In still other alternative embodiments, conditions suitable to cure invention film adhesive compositions may comprise subjecting invention film adhesive compositions to a pre-cure at temperatures high enough to increase the viscosity of the liquid adhesive and reduce tackiness but low enough to prevent a complete cure. Articles to which such pre-cured adhesive film compositions have been applied may then, at some later time, be subjected to a final cure as described above to give the fully cured adhesive.

The invention will now be described in greater detail by reference to the following non-limiting examples.

EXAMPLE 1

Formulations were prepared from m-phenoxybenzyl acrylate (MPBA) which is an exemplary monomer according to the present invention and tricyclodecanedimethanol diacrylate (TCDDMA) which was disclosed in U.S. Pat. No. 6,121,358. The structures of these monomers are shown below.

Various mixtures of these two monomers (see Table 1) were catalyzed with 2 wt % dicumyl peroxide.

TABLE 1

Tensile Adhesion Test Compositions

| Formulation | 1a | 1b | 1c | 1d | 1e |
|---|---|---|---|---|---|
| MPBA | 73.5% | 83.3% | 88.2% | 93.1% | 98% |
| TCDDMDA | 24.5% | 14.7% | 9.8% | 4.9% | 0 |
| Dicumyperoxide | 2% | 2% | 2% | 2% | 2% |

The compositions were cured between clean copper slugs (1000×400×150 mils) and aluminum studs (290 mil head diameter) at 200° C. for twenty minutes. The assemblies were allowed to cool to room temperature and then tested for tensile strength using a Sebastian III tensile tester. The results of these tests are summarized in Table 2.

TABLE 2

Tensile Adhesion Test Results
Stud Pull Value (pounds force)

| Part | 1a | 1b | 1c | 1d | 1e |
|---|---|---|---|---|---|
| 1 | 25 | 43 | 0 | 94 | 71 |
| 2 | 14 | 36 | 92 | 106 | 77 |
| 3 | 26 | 38 | 93 | 105 | 78 |
| 4 | 27 | 38 | 87 | 58 | 67 |
| 5 | 0 | 53 | 83 | 86 | 43 |
| 6 | 0 | 32 | 64 | 72 | 74 |
| 7 | 13 | 48 | 61 | 112 | 74 |
| 8 | 20 | 41 | 71 | 4 | 73 |
| 9 | 20 | 48 | 59 | 86 | 67 |
| 10 | 31 | 55 | 76 | 19 | 68 |
| Average | 17.6 | 43.2 | 68.6 | 74.2 | 69.2 |
| $\sum_{n-1}$ | 11 | 7.6 | 27 | 37 | 10 |

The adhesion increased for these mixtures as the concentration of MPBA in the mixture was raised. Without wishing to be bound by theory, it is believed that adhesion was improved with increasing MPBA because the shrinkage upon cure of the monomer mixtures was decreased. The TCDDMA is a highly reactive, relatively low equivalent weight, diacrylate monomer that exhibits considerable shrinkage upon cure.

The mixtures shown in Table 1 were not optimized for adhesion, but the results shown in Table 2 indicate that this approach has considerable potential. A more "fully formulated" system was prepared to further explore the use of the MPBA monomer. This test mixture was designated MV1258-13A and its composition is shown in Table 3.

TABLE 3

MV1258-13A Tensile Adhesion Test Compositions

| Component | Function | Percentage |
|---|---|---|
| X-Bismaleimide[1] | Co-monomer | 3.32 |
| MPBA[2] | New (invention) co-monomer | 6.19 |
| Polycyclic aliphatic acrylate[3] | Co-monomer | 6.20 |
| Ricon 130MA20[4] | Co-monomer | 1.00 |
| Silquest A-186[5] | Coupling Agent | 0.24 |
| QM-57[6] | Co-monomer | 2.40 |
| USP90MD[7] | Initiator | 0.65 |

TABLE 3-continued

MV1258-13A Tensile Adhesion Test Compositions

| Component | Function | Percentage |
|---|---|---|
| EA0018[8] | Silver flake filler | 40.0 |
| SF98[9] | Silver flake filler | 40.0 |

[1]Described in U.S. Pat. Nos. 6,034,194 and 6,034,195;
[2]m-phenoxybenzylacrylate
[3]Described in U.S. Pat. No. 6,211,320;
[4]Ricon Resins, Inc.;
[5]Osi Specialties;
[6]Rohm and Haas;
[7]Witco Corporation;
[8]Chemet Corporation;
[9]Degussa Corporation.

The MV 1258-13A paste formulation was compared in a battery of tests to Ablestik 8360 (a widely used competitive die attach adhesive). The results of those tests are summarized in Table 4.

TABLE 4

Comparison of MV1258-13 and Ablestik 8360

| Metric | 1258-13 | Ablestik 8360 | Units |
|---|---|---|---|
| 5 rpm Viscosity @ 25° C. | 10,076 | 7,618 | Centipoise |
| Thixotropic Index (0.5/5 rpm) | 6.18 | 5.81 | None |
| Potlife @ 25° C. | >24 | <24 | Hours |
| Adhesion on Ag plated Cu | | | |
| @ 25° C., Avg. (min.) | 96.8 (91.1) | 97.2 (77.1) | Kilograms force |
| @ 245° C., Avg. (min.) | 14.9 (11.6) | 8.1 (5.7) | |
| Adhesion on BTA-Cu | | | |
| @ 25° C., Avg. (min). | 84.1 (74.7) | 83.2 (27.7) | Kilograms force |
| @ 245° C., Avg. (min.) | 16.9 (12.3) | 7.6 (5.7) | |
| Adhesion on bar Cu | | | |
| @ 25° C., Avg. (min.) | 86.6 (80.8) | 86.3 (78.5) | Kilograms force |
| @ 245° C., Avg. (min.) | 20.8 (16.2) | 13.4 (8.9) | |
| 25° C. Adhesion after 1 min. @ 245° C. (wire bond simulation), Avg. (min.) | 88.2 (79.3) | 61.6 (49.1) | Kilograms force |
| Radius of Curvature (on Ag-Cu) | 0.44 ± 0.05 | 0.39 ± 0.04 | meters |
| Coefficient of Thermal Expansion | | | |
| below Tg | 45.8 | 52.0 | ppm/° C. |
| Above Tg | 156 | 170.0 | |
| Glass Transition Temperature | 29.4 | 16.9 | ° C. |
| Modulus of Elasticity @ 25° C. | 5.04 | 2.60 | GPa |
| Modulus of Elasticity @ 150° C. | 0.18 | 0.09 | GPa |
| Weight loss @ 250° C. (TGA) | 0.73 | 21.9 | % |
| Volume Resistivity | 9 × 10[5] | 1.7 × 10[4] | ohm-cm |
| Moisture Absorption (% wt. Gain) | | | |
| 24 hrs in 85/85 | 0.13 | 0.71 | % |
| 48 hrs in 85/85 | 0.13 | 0.86 | |
| 144 hrs in 85/85 | 0.13 | 0.87 | |
| 168 hrs in 85/85 | 0.13 | 0.85 | |

The MV1258-13A was found to have superior properties compared to the control paste. Even though the Ablestik 8360 had comparable room temperature die shear adhesion it was inferior at wire bond temperatures. It was also more seriously degraded by a one minute exposure to 245° C. (which was used to simulate real world wire bond conditions that would be required during the assembly process). Furthermore, the control material had much higher weight loss on cure and moisture absorption upon exposure to 85° C., 85% relative humidity moisture conditioning. The superior properties of the MV1258-13A were believed to be, in part, due to the use of the MPBA monomer.

EXAMPLE 2

Synthesis of 6-(2,5-Dioxo-2,5-dihydro-pyrrol-1-yl)-hexanoic Acid 2-(4'-{2-[6-(2,5-dioxo-2,5-dihydro-pyrrol-1-yl)-hexanoyloxy]-1-methyl-ethoxy}-biphenyl-4-yloxy)-propyl Ester -continued 4,4'-Biphenol (93.1 g, 0.5 mol), propylene carbonate (112.2 g, 1.1 mol), triethylamine (2.5 g), and xylene (200 mL) were placed into a 1000 mL round-bottom flask with a magnetic stirrer and condenser. This mixture was heated to reflux until no more gas was released (48 hours). The system was allowed to cool to room temperature, and a white solid product precipitated. The solid was filtered and washed with 200 mL of cold xylene. It was then dried in an oven at 70° C. to give a white solid. M.p: 185–187° C. Yield: 80%.

The solid from above (30.2 g, 0.1 mol), 6-maleimidocaproic acid (42.2 g, 0.2 mol), and methanesulfonic acid (3.0 g) were dissolved into 500 mL of toluene in a 1000 mL three-neck round-bottom flask. This mixture was heated to reflux while stirring. A Dean-Stark trap was used to collect the water generated from this reaction. After 12 hours of refluxing, 3.6 mL of water was collected.

The organic layer from this reaction was cooled to room temperature and washed with water three times. It was then passed thorough a thin layer of silica gel on a filtration funnel. The solvent was removed in vacuo to give a slightly yellow solid. Yield: 88%. M.p.: 90–92° C.

What is claimed is:

1. A compound represented by the following structure:

wherein:
  each Q is independently substituted or unsubstituted phenylene, substituted or unsubstituted cyclohexylene, substituted or unsubstituted naphthylene, or combinations of any two or more thereof;
  each X is independently —S(O)$_2$—N(R)—, —N(R)—, —C(O)—N(R)—, —O—C(O)—O—, —O—C(O)—N(R)—, —N(R)—C(O)—N(R)—, wherein R is —H or substituted or unsubstituted lower alkyl;
  each L is optional and, if present, is independently substituted or unsubstituted alkylene or substituted or unsubstituted oxyalkylene;
  each M is independently an ethylenically unsaturated crosslinkable moiety or saturated non-crosslinkable moiety;
  n and m are each independently an integer between 0–3, provided that one of m and n is at least 1; and
  k is 1 or 2.

2. A compound of claim 1, wherein M is an ethylenically unsaturated crosslinkable moiety.

3. A compound of claim 2, wherein M is an unsaturated anhydride group, (meth)acrylate group, maleimide group, nadimide group, itaconimide group, styrene group, vinyl ester group, vinyl ether group, or divinyl group.

4. A compound of claim 3, wherein M is a (meth)acrylate group.

5. A compound of claim 3, wherein M is a maleimide, nadimide, or itaconimide group.

6. A compound of claim 1 having the structure wherein p=0–15.

7. A compound of claim 1 having the structure

8. A compound of claim 1, wherein Q is phenylene, X is absent, m is 0, and k is 1.

9. A compound of claim 8 having the structure wherein b=1–10.

10. A compound of claim 8 having the structure wherein b=1–10 and p=0–15.

11. A compound of claim 8 having the structure wherein R is —H or optionally substituted alkyl.

12. A compound of claim 8 having the structure wherein R is —H or optionally substituted alkyl.

13. A low shrinkage adhesive composition comprising a compound according to claim 1 and a curing catalyst.

14. A composition according to claim 1, further comprising a maleimide, a nadimide, an itaconimide, or combinations of any two or more thereof, wherein the maleimide, nadimide, and itaconimide comprise, respectively, the structures I, II and III:

wherein:
m=1–15,
p=0–15,
each $R^2$ is independently selected from hydrogen or lower alkyl, and J is a monovalent or a polyvalent moiety comprising organic or organosiloxane radicals, and combinations of any two or more thereof.

15. A composition according to claim 14, wherein:
J is a monovalent or polyvalent radical selected from the group consisting of hydrocarbyl, substituted hydrocarbyl, heteroatom-containing hydrocarbyl, substituted heteroatom-containing hydrocarbyl, hydrocarbylene, substituted hydrocarbylene, heteroatom-containing hydrocarbylene, substituted heteroatom-containing hydrocarbylene, polysiloxane, polysiloxane-polyurethane block copolymer, and combinations of two or more thereof, optionally containing one or more linkers selected from the group consisting of a covalent bond, —O—, —S—, —NR—, —O—C(O)—, —O—C(O)—O—, —O—C(O)—NR—, —NR—C(O)—, —NR—C(O)—O—, —NR—C(O)—NR—, —S—C(O)—, —S—C(O)—O—, —S—C(O)—NR—, —O—S(O)$_2$—, —O—S(O)$_2$—O—, —O—S(O)$_2$—NR—, —O—S(O)—, —O—S(O)—O—, —O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR—, —NR—C(S)—, —NR—C(S)—O—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—O—, —NR—O—S(O)$_2$—NR—, —O—NR—S(O)—, —O—NR—S(O)—O—, —O—NR—S(O)—NR—, —O—NR—S(O)$_2$—O—, —O—NR—S(O)$_2$—NR—, —O—NR—S(O)$_2$—, —O—P(O)R$_2$—, —S—P(O)R$_2$—, —NR—P(O)R$_2$—, wherein each R is independently hydrogen, alkyl or substituted alkyl, and combinations of any two or more thereof.

16. A composition according to claim 14, wherein:
m=1–6,
p=0–6, and
J is
(a) saturated straight chain alkyl or branched chain alkyl, optionally containing substituents selected from hydroxy, alkoxy, carboxy, nitrile, cycloalkyl cycloalkenyl, or optionally substituted aryl moieties as substituents on the alkyl chain or as part of the backbone of the alkyl chain, and wherein the alkyl chains have up to about 20 carbon atoms;
(b) alkylene, oxyalkylene, alkenyl, alkenylene, oxyalkenylene, ester, or polyester, optionally containing substituents selected from hydroxy, alkoxy, carboxy, nitrile, cycloalkyl or cycloalkenyl;
(c) a siloxane having the structure —(C(R$^3$)$_2$)$_d$—[Si(R$^4$)$_2$—O]$_f$—Si(R$^4$)$_2$—(C(R$^3$)$_2$)$_e$—, —(C(R$^3$)$_2$)$_d$—C(R$^3$)—C(O)O—(C(R$^3$)$_2$)$_d$—[Si(R$^4$)$_2$—O]$_f$—Si(R$^4$)$_2$—(C(R$^3$)$_2$)$_e$—O(O)C—(C(R$^3$)$_2$)$_e$—, or —(C(R$^3$)$_2$)$_d$—C(R$^3$)—O(O)C—(C(R$^3$)$_2$)$_d$—[Si(R$^4$)$_2$—O]$_f$—Si(R$^4$)$_2$—(C(R$^3$)$_2$)$_e$—C(O)O—(C(R$^3$)$_2$)$_e$— wherein,
each $R^3$ is independently hydrogen, alkyl or substituted alkyl,
each $R^4$ is independently hydrogen, lower alkyl or aryl,
d=1–10, e=1–10, and  
f=1–50;  
(d) a polyalkylene oxide having the structure:

wherein:  
each R is independently hydrogen, alkyl or substituted alkyl,  
r=1–10,  
s=1–10, and  
f is as defined above;  
(e) aromatic groups having the structure:

wherein each Ar is a monosubstituted, disubstituted or trisubstituted aromatic or heteroaromatic ring having in the range of 3 up to 10 carbon atoms, and Z is:  
(i) saturated straight chain alkylene or branched chain alkylene, optionally containing saturated cyclic moieties as substituents on the alkylene chain or as part of the backbone of the alkylene chain, or  
(ii) polyalkylene oxides having the structure:

wherein:  
each R is independently defined as above,  
r=1–10,  
s=1–10, and  
q=1–50;  
(f) di- or tri-substituted aromatic moieties having the structure:

wherein:  
each R is independently defined as above,  
t=2–10,  
a=2–10, and  
Ar is as defined above;  
(g) aromatic groups having the structure:

-continued wherein:  
t=2–10,  
u=1, 2 or 3,  
g=1 up to about 50,  
each R is independently defined as above,  
each Ar is as defined above,  
E is —O— or —$NR^5$—, wherein $R^5$ is hydrogen or lower alkyl; and  
W is  
(i) straight or branched chain alkyl, alkylene, oxyalkylene, alkenyl, alkenylene, oxyalkenylene, ester, or polyester, optionally containing substituents selected from hydroxy, alkoxy, carboxy, nitrile, cycloalkyl or cycloalkenyl,  
(ii) a siloxane having the structure —$(C(R^3)_2)_d$—[$Si(R^4)_2$—O]$_f$—$Si(R^4)_2$—$(C(R^3)_2)_e$—, —$(C(R^3)_2)_d$—$C(R^3)$—C(O)O—$(C(R^3)_2)_d$—[Si(R^4)_2$—O]$_f$—$Si(R^4)_2$—$(C(R^3)_2)_e$—O(O)C—$(C(R^3)_2)_e$—, or —$(C(R^3)_2)_d$—$C(R^3)$ —O(O)C—$(C(R^3)_2)_d$—[Si(R^4)_2$—O]$_f$—$Si(R^4)_2$—$(C(R^3)_2)_e$—C(O)O—$(C(R^3)_2)_e$— wherein,  
each $R^3$ is independently hydrogen, alkyl or substituted alkyl,  
each $R^4$ is independently hydrogen, lower alkyl or aryl,  
d=1–10,  
e=1–10, and  
f=1–50; or  
(iii) a polyalkylene oxide having the structure:

wherein:  
each R is independently defined as above,  
r=1–10,  
s 1–10, and  
f is defined as above;  
optionally containing substituents selected from hydroxy, alkoxy, carboxy, nitrile, cycloalkyl or cycloalkenyl;  
(h) a urethane group having the structure:

wherein:  
each $R^6$ is independently hydrogen or lower alkyl;  
each $R^7$ is independently an alkyl, aryl, or arylalkyl group having 1 to 18 carbon atoms;  
each $R^8$ is an alkyl or alkyloxy chain having up to about 100 atoms in the chain, optionally substituted with Ar;  
U is —O—, —S—, —N(R)—, or —P(L)$_{1,2}$— wherein R as defined above, and wherein each L is independently =O, =S, —OR or —R; and  
v=0–50;  
(i) polycyclic alkenyl; or  
(j) mixtures of any two or more thereof.  
17. A composition according to claim 16, wherein the maleimide, nadimide, itaconimide, or combination thereof is liquid at ambient temperature.

18. A low shrinkage thermosetting resin composition comprising:
   A) a compound according to claim 1,
   B) a maleimide, a nadimide, an itaconimide, or combinations of any two or more thereof,
   C) a coupling agent, and
   D) a cure initiator.

19. A resin composition according to claim 18, wherein the maleimide, nadimide, and itaconimide comprise, respectively, the structures I, II and III:

wherein:
   m=1–15,
   p=0–15,
   each $R^2$ is independently selected from hydrogen or lower alkyl, and
   J is a monovalent or a polyvalent moiety comprising organic or organosiloxane radicals, and combinations thereof.

20. A composition according to claim 19, wherein:
J is a monovalent or polyvalent radical selected from the group consisting of hydrocarbyl, substituted hydrocarbyl, heteroatom-containing hydrocarbyl, substituted heteroatom-containing hydrocarbyl, hydrocarbylene, substituted hydrocarbylene, heteroatom-containing hydrocarbylene, substituted heteroatom-containing hydrocarbylene, polysiloxane, polysiloxane-polyurethane block copolymer, and combinations of two or more thereof, optionally containing one or more linkers selected from the group consisting of a covalent bond, —O—, —S—, —NR—, —O—C(O)—, —O—C(O)—O—, —O—C(O)—NR—, —NR—C(O)—, —NR—C(O)—O—, —NR—C(O)—NR—, —S—C(O)—, —S—C(O)—O—, —S—C(O)—NR—, —O—S(O)$_2$—, —O—S(O)$_2$—O—, —O—S(O)$_2$—NR—, —O—S(O)—, —O—S(O)—O—, —O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR—, —NR—C(S)—, —NR—C(S)—O—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—O—, —NR—O—S(O)$_2$—NR—, —O—NR—S(O)—, —O—NR—S(O)—O—, —O—NR—S(O)—NR—, —O—NR—S(O)$_2$—O—, —O—NR—S(O)$_2$—NR—, —O—NR—S(O)$_2$—, —O—P(O)R$_2$—, —S—P(O)R$_2$—, —NR—P(O)R$_2$—, wherein each R is independently hydrogen, alkyl or substituted alkyl, and combinations of any two or more thereof.

21. A composition according to claim 19, wherein:
m=1–6,
p=0–6, and
J is
   (a) saturated straight chain alkyl or branched chain alkyl, optionally containing substituents selected from hydroxy, alkoxy, carboxy, nitrile, cycloalkyl cycloalkenyl, or optionally substituted aryl moieties as substituents on the alkyl chain or as part of the backbone of the alkyl chain, and wherein the alkyl chains have up to about 20 carbon atoms;
   (b) alkylene, oxyalkylene, alkenyl, alkenylene, oxyalkenylene, ester, or polyester, optionally containing substituents selected from hydroxy, alkoxy, carboxy, nitrile, cycloalkyl or cycloalkenyl;
   (c) a siloxane having the structure —(C(R$^3$)$_2$)$_d$—[Si(R$^4$)$_2$—O]$_f$—Si(R$^4$)$_2$—(C(R$^3$)$_2$)$_e$—, —(C(R$^3$)$_2$)$_d$—C(R$^3$)—C(O)O—(C(R$^3$)$_2$)$_d$—[Si(R$^4$)$_2$—O]$_f$—Si(R$^4$)$_2$—(C(R$^3$)$_2$)$_e$—O(O)C—(C(R$^3$)$_2$)$_e$—, or —(C(R$^3$)$_2$)$_d$—C(R$^3$)—O(O)C—(C(R$^3$)$_2$)$_d$—[Si(R$^4$)$_2$—O]$_f$—Si(R$^4$)$_2$—(C(R$^3$)$_2$)$_e$—C(O)O—(C(R$^3$)$_2$)$_e$— wherein,
   each $R^3$ is independently hydrogen, alkyl or substituted alkyl,
   each $R^4$ is independently hydrogen, lower alkyl or aryl,
   d=1–10,
   e=1–10, and
   f=1–50;
   (d) a polyalkylene oxide having the structure:

wherein:
   each R is independently hydrogen, alkyl or substituted alkyl,
   r=1–10,
   s=1–10, and
   f is as defined above;
   (e) aromatic groups having the structure:

wherein each Ar is a monosubstituted, disubstituted or trisubstituted aromatic or heteroaromatic ring having in the range of 3 up to 10 carbon atoms, and Z is:
      (i) saturated straight chain alkylene or branched chain alkylene, optionally containing saturated cyclic moieties as substituents on the alkylene chain or as part of the backbone of the alkylene chain, or (ii) polyalkylene oxides having the structure:

wherein:
each R is independently defined as above,
r=1–10,
s=1–10, and
q=1–50;

(f) di- or tri-substituted aromatic moieties having the structure:

wherein:
each R is independently defined as above,
t=2–10,
a=2–10, and
Ar is as defined above;

(g) aromatic groups having the structure:

wherein:
t=2–10,
u=1, 2 or 3,
g=1 up to about 50,
each R is independently defined as above,
each Ar is as defined above,
E is —O— or —NR$^5$—, wherein R$^5$ is hydrogen or lower alkyl; and
W is
(i) straight or branched chain alkyl, alkylene, oxyalkylene, alkenyl, alkenylene, oxyalkenylene, ester, or polyester, optionally containing substituents selected from hydroxy, alkoxy, carboxy, nitrile, cycloalkyl or cycloalkenyl,
(ii) a siloxane having the structure —(C(R$^3$)$_2$)$_d$—[Si(R$^4$)$_2$—O]$_f$—Si(R$^4$)$_2$—(C(R$^3$)$_2$)$_g$—, —(C(R$^3$)$_2$)$_d$—(C(R$^3$)—C(O)O—(C(R$^3$)$_2$)$_d$—[Si(R$^4$)$_2$—O]$_f$—Si(R$^4$)$_2$—(C(R$^3$)$_2$)$_e$—O(O)C—(C(R$^3$)$_2$)$_e$—, or —(C(R$^3$)$_2$)$_d$—C(R$^3$)—O(O)C—(C(R$^3$)$_2$)$_d$—[Si(R$^4$)$_2$—O]$_f$—Si(R$^4$)$_2$—(C(R$^3$)$_2$)$_e$—C(O)O—(C(R$^3$)$_2$)$_e$— wherein,
each R$^3$ is independently hydrogen, alkyl or substituted alkyl,
each R$^4$ is independently hydrogen, lower alkyl or aryl, d=1–10,
e=1–10, and
f=1–50; or (iii) a polyalkylene oxide having the structure:

wherein:
each R is independently defined as above,
r=1–10,
s=1–10, and
f is defined as above;
optionally containing substituents selected from hydroxy, alkoxy, carboxy, nitrile, cycloalkyl or cycloalkenyl;

(h) a urethane group having the structure:

wherein:
each R$^6$ is independently hydrogen or lower alkyl;
each R$^7$ is independently an alkyl, aryl, or arylalkyl group having 1 to 18 carbon atoms;
each R$^8$ is an alkyl or alkyloxy chain having up to about 100 atoms in the chain, optionally substituted with Ar;
U is —O—, —S—, —N(R)—, or —P(L)$_{1,2}$— wherein R as defined above, and wherein each L is independently =O, =S, —OR or —R; and
v=0–50;

(i) polycyclic alkenyl; or (j) mixtures of any two or more thereof.

22. A composition according to claim 21, wherein the maleimide, nadimide, itaconamide, or combination thereof is liquid at ambient temperature.

23. A low shrinkage formulation comprising:

in the range of about 10 up to 80 weight percent of a thermosetting resin composition according to claim 21, and in the range of about 20 up to 90 weight percent of a filler.

24. A formulation according to claim 23, wherein the filler is conductive.

25. A formulation according to claim 24, wherein the conductive filler is electrically conductive.

26. A formulation according to claim 24, wherein the conductive filler is thermally conductive.

27. A formulation according to claim 23, further comprising an acrylate derivative of oligomers of optionally substituted cyclopentadiene.

28. A method for reducing the shrinkage upon cure of a thermoset resin composition, the method comprising combining the resin with a compound according to claim 1.

29. The method according to claim 28, wherein the thermosetting resin composition further comprises a maleimide, a nadimide, an itaconimide, or combinations of any two or more thereof, wherein the maleimide, nadimide, and itaconimide comprise, respectively, the structures I, II and III:

wherein:
m=1–15,
p=0–15,
each $R^2$ is independently selected from hydrogen or lower alkyl, and
J is a monovalent or a polyvalent moiety comprising organic or organosiloxane radicals, and combinations thereof.

30. The method according to claim 29, wherein:
J is a monovalent or polyvalent radical selected from the group consisting of hydrocarbyl, substituted hydrocarbyl, heteroatom-containing hydrocarbyl, substituted heteroatom-containing hydrocarbyl, hydrocarbylene, substituted hydrocarbylene, heteroatom-containing hydrocarbylene, substituted heteroatom-containing hydrocarbylene, polysiloxane, polysiloxane-polyurethane block copolymer, and combinations of two or more thereof, optionally containing one or more linkers selected from the group consisting of a covalent bond, —O—, —S—, —NR—, —O—C(O)—, —O—C(O)—O—, —O—C(O)—NR—, —NR—C(O)—, —NR—C(O)—O—, —NR—C(O)—NR—, —S—C(O)—, —S—C(O)—O—, —S—C(O)—NR—, —O—S(O)$_2$—, —O—S(O)$_2$—O—, —O—S(O)$_2$—NR, —O—S(O)—, —O—S(O)—O—, —O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR—, —NR—C(S)—, —NR—C(S)—O—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—O—, —NR—O—S(O)$_2$—NR—, —O—NR—S(O)—, —O—NR—S(O)—O—, —O—NR—S(O)—NR—, —O—NR—S(O)$_2$—O—, —O—NR—S(O)$_2$NR—, —O—NR—S(O)$_2$—, —O—P(O)R$_2$—, —S—P(O)R$_2$—, —NR—P(O)R$_2$—, wherein each R is independently hydrogen, alkyl or substituted alkyl, and combinations of any two or more thereof.

31. A method according to claim 29, wherein:
m=1–6,
p=0–6, and
J is
(a) saturated straight chain alkyl or branched chain alkyl, optionally containing substituents selected from hydroxy, alkoxy, carboxy, nitrile, cycloalkyl cycloalkenyl, or optionally substituted aryl moieties as substituents on the alkyl chain or as part of the backbone of the alkyl chain, and wherein the alkyl chains have up to about 20 carbon atoms;
(b) alkylene, oxyalkylene, alkenyl, alkenylene, oxyalkenylene, ester, or polyester, optionally containing substituents selected from hydroxy, alkoxy, carboxy, nitrile, cycloalkyl or cycloalkenyl;
(c) a siloxane having the structure —(C(R$^3$)$_2$)$_d$—[Si(R$^4$)$_2$—O]$_f$—Si(R$^4$)$_2$—(C(R$^3$)$_2$)$_e$—, —(C(R$^3$)$_2$)$_d$—(C(R$^3$))—C(O)O—(C(R$^3$)$_2$)$_d$—[Si(R$^4$)$_2$—O]$_f$—Si(R$^4$)$_2$—(C(R$^3$)$_2$)$_e$—O(O)C—(C(R$^3$)$_2$)$_e$—, or —(C(R$^3$)$_2$)$_d$—C(R$^3$)—O(O)C —(C(R$^3$)$_2$)$_d$—[Si(R$^4$)$_2$—O]$_f$—Si(R$^4$)$_2$—(C(R$^3$)$_2$)$_e$—C(O)O—(C(R$^3$)$_2$)$_e$—
wherein,
each $R^3$ is independently hydrogen, alkyl or substituted alkyl,
each $R^4$ is independently hydrogen, lower alkyl or aryl,
d=1–10,
e=1–10, and
f=1–50;
(d) a polyalkylene oxide having the structure:

wherein:
each R is independently hydrogen, alkyl or substituted alkyl,
r=1–10,
s=1–10, and
f is as defined above;
(e) aromatic groups having the structure:

wherein each Ar is a monosubstituted, disubstituted or trisubstituted aromatic or heteroaromatic ring having in the range of 3 up to 10 carbon atoms, and Z is:
(i) saturated straight chain alkylene or branched chain alkylene, optionally containing saturated cyclic moieties as substituents on the alkylene chain or as part of the backbone of the alkylene chain, or
(ii) polyalkylene oxides having the structure:

wherein:
each R is independently defined as above,
r=1–10,
s=1–10, and
q=1–50;

(f) di- or tri-substituted aromatic moieties having the structure:

wherein:
each R is independently defined as above,
t=2–10,
a=2–10, and
Ar is as defined above;

(g) aromatic groups having the structure:

wherein:
t=2–10,
u 1, 2 or 3,
g=1 up to about 50,
each R is independently defined as above,
each Ar is as defined above,
E is —O— or —NR$^5$—, wherein R$^5$ is hydrogen or lower alkyl; and
W is
(i) straight or branched chain alkyl, alkylene, oxyalkylene, alkenyl, alkenylene, oxyalkenylene, ester, or polyester, optionally containing substituents selected from hydroxy, alkoxy, carboxy, nitrile, cycloalkyl or cycloalkenyl,
(ii) a siloxane having the
each R is independently defined as above,
r=1–10,
s=1–10, and
f is defined above;
optionally containing substituents selected from hydroxy, alkoxy, carboxy, nitrile, cycloalkyl or cycloalkenyl;

(h) a urethane group having the structure:

wherein:
each R$^6$ is independently hydrogen or lower alkyl;
each R$^7$ is independently an alkyl, aryl, or arylalkyl group having 1 to 18 carbon atoms;
each R$^8$ is an alkyl or alkyloxy chain having up to about 100 atoms in the chain, optionally substituted with Ar;
U is —O—, —S—, —N(R)—, or —P(L)$_{1,2}$— wherein R as defined above, and wherein each L is independently =O, =S, —OR or —R; and
v=0–50;

(i) polycyclic alkenyl; or (j) mixtures of any two or more thereof.

32. The method according to claim 31, wherein the maleimide, nadimide, itaconimide, or combination thereof is liquid at ambient temperature.

33. A method for improving adhesive strength of a thermosetting resin composition, the method comprising combining the resin with a compound according to claim 1.

34. A method for the preparation of a low shrinkage thermosetting resin composition, the method comprising combining the resin with a compound according to claim 1.

35. A method for attaching a semiconductor device to a substrate, the method comprising curing a composition according to claim 18 positioned between and contacting a surface of the device and a surface of the substrate.

36. A method for improving the bond between a semiconductor device and a substrate, the method comprising
(a) applying an adhesive composition comprising a compound according to claim 1 to the surface of the device and/or the surface of the substrate;
(b) contacting the surface of the device with the surface of the substrate, and thereafter
(c) subjecting the adhesive composition to a temperature sufficient to cure the adhesive composition,
whereby shrinkage of the thermoset resin upon cure is reduced.

37. An adhesive film formulation comprising:
(a) a thermoset resin composition comprising a compound according to claim 1, and
(b) a thermoplastic elastomer that is a block copolymer having at least one unit of the general formula (A-B) or (A-B-A), wherein A is a non-elastomeric polymer block and B is an elastomeric polymer block that is the polymerization product of optionally substituted olefin monomers and/or optionally substituted conjugated diene monomers.

38. A method for adhesively attaching a device to a substrate, the method comprising curing an adhesive film formulation according to claim 37 positioned between and contacting a surface of the device and a surface of the substrate.

39. A method according to claim 38, wherein the device is a semiconductor die and the substrate is a lead frame.

40. An assembly comprising a device adhered to a substrate by the method of claim 38.

* * * * *

UNITED STATES PATENT AND TRADEMARK OFFICE
CERTIFICATE OF CORRECTION

PATENT NO. : 6,963,001 B2  
APPLICATION NO. : 10/367360  
DATED : November 8, 2005  
INVENTOR(S) : S. Dershem et al.

Page 1 of 1

It is certified that error appears in the above-identified patent and that said Letters Patent is hereby corrected as shown below:

Column 6, line 43, delete "while" and insert --wherein--.

Column 11, line 20, delete "aminocyclo alkyl" and insert --aminocycloalkyl--.

Column 13, bridging lines 44 and 45, delete "-$C(R^3)_2)_e$)-".

Column 14, lines 49, 50 and 51, delete all five occurrences of "tert" and insert --*tert*--.

Column 32, beginning of line 22, claim 31 delete "$(C(R^3)$" and insert --$C(R^3)$--.

Column 33, line 49, claim 31 after "having the" insert --structure —$(C(R^3)_2)_d$) -$[Si(R^4)_2-O]_f$-$Si(R^4)_2$-$(C(R^3)_2)_e$-, -$(C(R^3)_2)_d$-$C(R^3)$-$C(R^3)$-$C(O)O$-$(C(R^3)_2)_d$-$[Si(R^4)_2-O]_f$ -$Si(R^4)_2$-$(C(R^3)_2)_e$-$O(O)C$-$(C(R^3)_2)_e$-, or –$(C(R^3)_2)_d$-$C(R^3)$-$O(O)C$-$(C(R^3)_2)_d$-$[Si(R^4)_2$ -$O]_f$-$Si(R^4)_2$-$(C(R^3)_2)_e$-$C(O)O$-$(C(R^3)_2)_e$- wherein, each $R^3$ is independently hydrogen, alkyl or substitute alkyl, each $R^4$ is independently hydrogen, lower alkyl or aryl, d = 1-10, c = 1-10, and f = 1-50; or (iii) a polyalkylene oxide having the structure: -$[(CR_2)_r$-$O$-$]_f$-$(CR_2)_s$- wherein:--

Signed and Sealed this

Twentieth Day of May, 2008

JON W. DUDAS  
*Director of the United States Patent and Trademark Office*